(12) United States Patent
Bengi

(10) Patent No.: US 7,617,611 B2
(45) Date of Patent: Nov. 17, 2009

(54) TOOL FOR IDENTIFYING NON-CONFORMITIES

(75) Inventor: Tarkan Bengi, Biel (CH)

(73) Assignee: Philip Morris USA Inc., Richmond, VA (US)

( * ) Notice: Subject to any disclaimer, the term of this patent is extended or adjusted under 35 U.S.C. 154(b) by 327 days.

(21) Appl. No.: 11/699,499

(22) Filed: Jan. 30, 2007

(65) Prior Publication Data

US 2007/0175058 A1 Aug. 2, 2007

(30) Foreign Application Priority Data

Jan. 31, 2006 (EP) .................................. 06250520

(51) Int. Cl.
*G01B 5/20* (2006.01)
(52) U.S. Cl. .................... 33/561.2; 33/561.1; 33/562
(58) Field of Classification Search ............... 33/561.2, 33/561.1, 562, 514.1
See application file for complete search history.

(56) References Cited

U.S. PATENT DOCUMENTS

| | | | | |
|---|---|---|---|---|
| 1,282,772 | A | | 10/1918 | Dinhofer |
| 1,438,681 | A | * | 12/1922 | Bath ........................ 33/555.2 |
| 1,881,651 | A | * | 10/1932 | Judge ......................... 33/562 |
| 2,103,606 | A | * | 12/1937 | Abrahamsohn et al. ..... 324/115 |
| 3,127,899 | A | * | 4/1964 | Lloyd et al. ................. 131/108 |
| 3,407,507 | A | * | 10/1968 | Brubaker ................... 33/555.4 |
| 3,800,421 | A | * | 4/1974 | Sauer et al. .................... 33/22 |
| 3,905,366 | A | * | 9/1975 | Callahan et al. ............. 604/209 |
| 3,967,383 | A | | 7/1976 | Collins |
| 4,794,704 | A | * | 1/1989 | Calcagni et al. ............... 33/367 |
| 5,131,162 | A | * | 7/1992 | Miller ......................... 33/562 |
| 5,515,614 | A | * | 5/1996 | Wing .......................... 33/548 |
| 5,617,644 | A | * | 4/1997 | Bonelli ........................ 33/548 |
| D398,251 | S | * | 9/1998 | Martinez .................... D10/64 |
| 6,044,572 | A | * | 4/2000 | Sore et al. .................. 33/555.4 |
| D494,485 | S | * | 8/2004 | Schiene et al. .............. D10/71 |
| 6,904,941 | B2 | * | 6/2005 | Howard ..................... 138/167 |
| 7,111,411 | B2 | * | 9/2006 | Knopfle et al. ................ 33/562 |
| 2005/0072014 | A1 | | 4/2005 | Saunders |

FOREIGN PATENT DOCUMENTS

GB 1226055 A 3/1971

OTHER PUBLICATIONS

Written Opinion dated Apr. 24, 2006 for EP 06250520.1-2213.

* cited by examiner

*Primary Examiner*—G. Bradley Bennett
*Assistant Examiner*—Tania C Courson
(74) *Attorney, Agent, or Firm*—Buchanan Ingersoll & Rooney PC

(57) ABSTRACT

A tool for identifying a non-conformity on a curved surface of an object, in particular on the circumferential surface of a cigarette, comprises a curved surface having a scale along a direction of curvature and a viewing portion associated with the scale through which, in use, at least part of the curved surface of the object is visible.

15 Claims, 2 Drawing Sheets

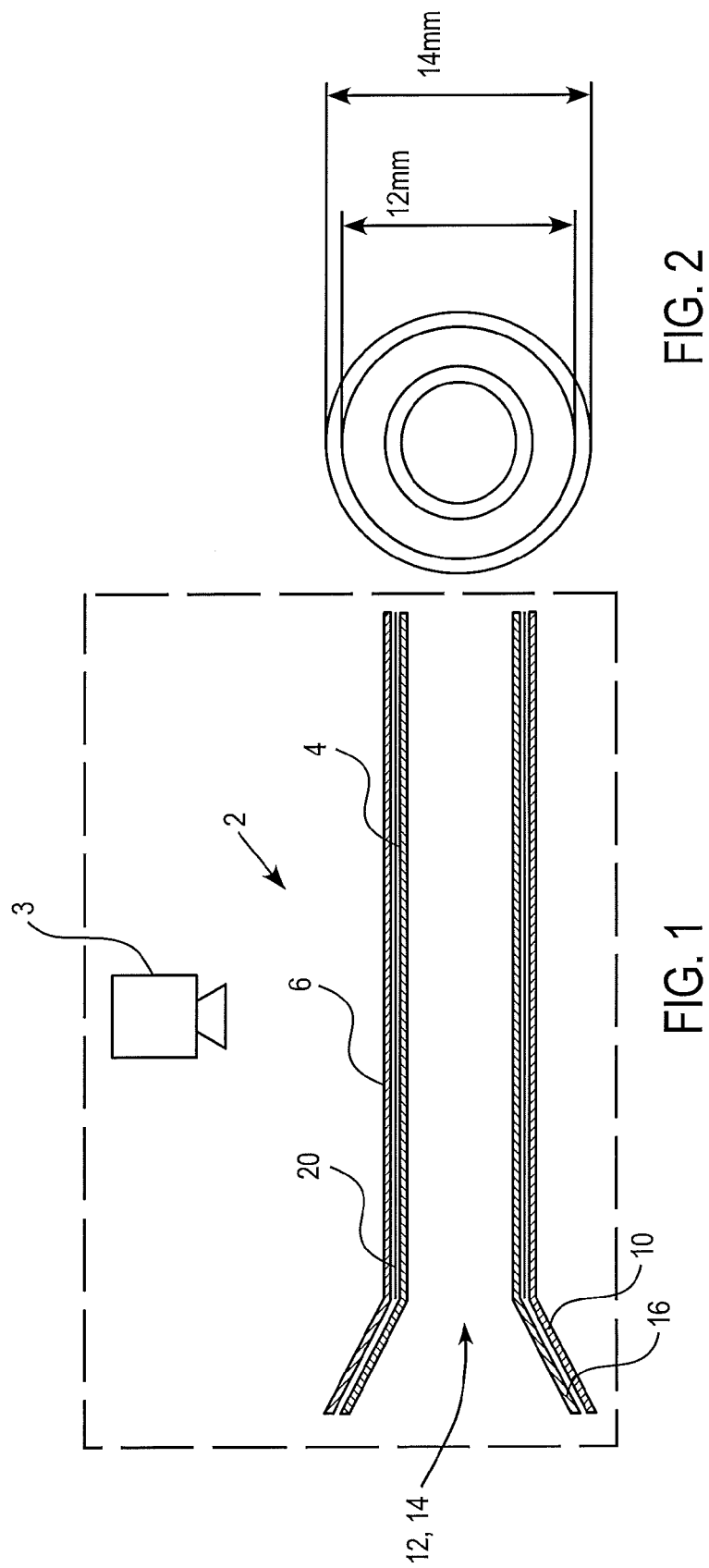

TOOL FOR IDENTIFYING NON-CONFORMITIES

CROSS REFERENCE TO RELATED APPLICATION

This application claims priority under 35 U.S.C. §119 to European Application No. 06 250 520.1, filed Jan. 31, 2006, the entire contents of which is hereby incorporated by reference.

The present invention relates to a tool for identifying a non-conformity on a curved surface of an object, in particular a non-conformity on the circumferential surface of a cigarette, and to the use of such a tool.

While the focus is on identifying a non-conformity, the tool of the present invention is generally suitable to assess one or more quantitative or qualitative parameters on a curved surface. Advantageously, the assessment comprises the determination of at least one parameter and evaluation of the parameter against a pre-determined standard. The parameter may or may not conform to the standard. Preferably, the tool is used to identify one or more-non-conformities on a curved surface of an object.

Quality control systems for maintaining standards in manufactured products are well known. Typically such systems involve the periodic inspection of randomly selected samples of the manufactured product in order to assess whether they comply with one or more pre-determined requirements. Depending on the degree or extent of compliance, the identification of a non-conformity in a sample of the manufactured product may lead to a quantity of the product being rejected, the manufacturing process being adjusted and/or to the replacement of manufacturing equipment or raw materials.

During the manufacture of cigarettes, the curved circumferential surface of randomly selected cigarettes is typically inspected as part of a visual quality audit in order to identify and assess non-conformities such as, for example, tears or stains on the wrapper. The identification and assessment of such non-conformities commonly involves comparing an area of interest to a scale to determine whether one or more parameters of the area of interest, such as size or colour, fall within a pre-determined acceptable range. In some cases, a number of different ranges may be used in order to classify the inspected cigarette according to the seriousness of the non-conformities identified thereon and the outcome of the visual quality audit made dependent on this classification.

Even with precisely defined visual quality standards, a certain degree of subjective judgment by the person making the inspection is unavoidable. It would therefore be beneficial to use a tool that minimises the subjectivity of the judgment.

Conventional hand-held tools for measuring lengths and distances, such as rulers, typically include a rigid planar surface having at least one straight edge that is marked at regular intervals to form a scale. While such tools are suitable for the measurement of lengths and distances on planar surfaces, they are not easily adapted to the measurement of lengths or distances on curved surfaces. For example, to measure a non-conformity such as a tear on the curved circumferential surface of a cigarette using a ruler, the cigarette and ruler must be rotated relative to one another during the measurement. As well as being awkward and impractical, the relative rotation of the ruler and cigarette may lead to inaccuracies in the measurement being taken.

It would be desirable, therefore, to provide a tool for identifying non-conformities on a curved surface of an object, such as a cigarette.

According to the present invention there is provided a tool for identifying a non-conformity on a curved surface of an object comprising: a curved surface having a scale extending along a direction of curvature, the scale enabling a measurement along the direction of curvature; and a viewing portion associated with the scale through which, in use, at least part of the curved surface of the object is visible.

By providing a tool with a curved surface, which, in use, may be placed over a curved surface of an object, and a scale extending along a direction of curvature of the curved surface, which, in use, may be lined up with an area of interest on the curved surface of the object, tools according to the present invention advantageously enable the direct, rapid and precise identification of non-conformities on curved surfaces. Quantitative or qualitative parameters which may be assessed with tools according to the invention may relate to an entire object or parts thereof and include, for example, length, circumference, and colour. Preferably, the assessment includes the judgment of whether the parameter is within a desired range or not.

Placement of the curved surface of the tool over an area of interest on the curved surface of an object allows a measurement to be established directly, without the need to move the tool and object relative to one another. The viewing portion associated with the scale enables the curved surface of the object to be seen through the curved surface of the tool so that, in use, the scale may be positioned on or against an area of interest on the curved surface of the object in order to carry out an assessment.

An 'area of interest' on the curved surface of an object is an area that is inspected to measure a particular parameter of the object and to optionally evaluate its conformity. 'Non-conformity' is used throughout the specification to mean any abnormality, anomaly, distortion or irregularity, which means that the inspected area of interest does not comply with pre-determined quality requirements. For example, where the curved surface is the circumferential surface of a cigarette, non-conformities that may be identified using tools according to preferred embodiments of the present invention include, but are not limited to, radial or axial compressions of the rod end, tears or holes in the cigarette paper or tipping, torn or ragged rod ends due to improper cuts, smeared or dirty cigarette paper or tipping, oil or tobacco spots on the rod, yellowish or wrinkled rods, ink smears on printed areas, low print intensity, non-uniform text or logos, scratched tipping, tipping misalignment or wrinkling and rough cut tipping.

Advantageously, the dimensions of the tool are designed to correspond to those of the object and its curved surface and to enable assessment of the desired parameters without damaging the object. For example, a preferred tool according to the invention is tubular in shape to assess areas of interest on the circumferential surface of a rod-shaped cylindrical object, for example a cigarette. Preferably, the diameter of the tool is slightly larger than the external diameter of the cigarette.

Tools according to the invention may comprise one or more scales of the same or different types.

Preferably, the tool comprises at least one size scale for measuring an area of interest on a curved surface of an object. The size scale may, for example, comprise a plurality of markings provided at regular intervals in the direction of curvature of the curved surface of the tool.

Preferably, the tool comprises at least one colour scale for assessing the colour of an area of interest on a curved surface of an object. For example, this may be a colour scale to assess the colour of the tipping paper, the cigarette paper or of print on the cigarette paper or tipping paper of a cigarette.

Tools according to the present invention may comprise one or more size scales, one or more colour scales or a combination of one or more size scales and one or more colour scales.

According to the present invention there is also provided a tool for identifying a non-conformity on a curved surface of an object comprising: a curved surface having a colour scale for assessing the colour of an area of interest, a size scale for assessing the size of an area of interest and at least one viewing portion associated with the scales through which, in use, at least part of the curved surface of the object is visible.

The provision of a size scale and a colour scale advantageously enables more than one property of any area of interest, of a non-conformity and/or different types of non-conformities on a curved surface of an object to be assessed using the same tool. For example, tools according to the present invention may advantageously be used to assess both the size of an area of interest on a curved surface of an object, such as a tear in the wrapper of a cigarette, and also to assess the colour of the same or a different area of interest on the curved surface of the object, such as a stain on the wrapper of a cigarette. The present invention may thereby eliminate the need for multiple tools to be employed in a visual quality audit and simplify the procedure for identifying multiple non-conformities on a curved surface of an object.

The scale may be etched into, printed on or otherwise applied directly to the curved surface of the tool. Alternatively, the scale may be provided on, for example, a separate film sheet to be used in conjunction with the tool, for example, by wrapping and fixing the film around the curved surface of the tool. Films having different scales may be interchanged as desired. Alternatively, the film itself may be rolled and fixed to itself in order to provide the curved surface of the tool.

The curved surface of the tool may be formed of any suitable material such as, for example, cardboard, metal, glass or plastic.

The viewing portion may be a transparent region of the curved surface of the tool or a hole therein.

Preferably, at least a portion of the curved surface of the tool is transparent, more preferably substantially the entire curved surface of the tool is transparent, which facilitates alignment of an area of interest on a curved surface of an object with a respective scale.

Preferably, the tool comprises a hollow circularly cylindrical tube having at least one open end, into which, in use, a cylindrical object may be inserted. Preferably, at least a portion of the circumferential surface of the tube is transparent. More preferably, substantially the entire circumferential surface of the tube is transparent.

Tools according to the present invention comprising cylindrical tubes are useful for the identification of non-conformities on the curved circumferential surface of circularly cylindrical objects, in particular cigarettes. In use, a cigarette may be inserted into the hollow cylindrical tube of the tool of the invention and the cigarette and tube then rotated relative to one another until an area of interest on the circumferential surface of the cigarette is aligned with an appropriate scale for assessment. Preferably, the open end of the cylindrical tube is funnelled in order to facilitate insertion of a cylindrical object into the tube. If desired, the other end of the tube may be closed, in order to help retain the object within the tube during the assessment of an area of interest.

In a particularly preferred embodiment of the invention, the tool comprises two concentric circularly cylindrical tubes. Preferably these tubes are rotatable relative to one another about their longitudinal axes and slidable relative to one another along their longitudinal axes. Preferably, at least a portion of the circumferential surface of each tube is transparent. More preferably, substantially the entire circumferential surface of each tube is transparent.

In use, a circularly cylindrical object, such as a cigarette, may be inserted into the inner tube of the two concentric cylindrical tubes. The two tubes may then be rotated and slid relative to one another in order to line up an area of interest on the curved circumferential surface of the object with an appropriate scale provided on the outer concentric tube or on, for example, a layer of film, preferably transparent film, or other material provided between the two concentric cylinders. The provision of a pair of concentric tubes may thereby advantageously simplify the procedure of aligning the area of interest with the scale since it avoids the need to rotate the object itself, once it has been inserted into the tool. Additionally, the inner cylindrical tube protects the outer cylindrical tube bearing the scale, or the scale itself when disposed between the two cylindrical tubes, from contact with the curved surface of the object.

In an alternative embodiment of the invention, the inner cylindrical tube and the outer cylindrical tube are affixed to each other. In this embodiment the cigarette and the entire tool are moved relative to each other in order to align an area of interest on the curved circumferential surface of the cigarette with the scale.

The size scale on the curved surface of the tool may be provided by one or more distance markings which extend along the curvature of the surface. The markings may, for example, be a continuous ruler scale or may provide certain limits of the ranges of the size of a particular non-conformity, defined by the ranges required by the visual quality audit, so that it may easily be determined whether or not an area of interest on a curved surface of an object is or is not a non-conformity and/or into which range the non-conformity falls. Alternatively or in addition, a size scale on the curved surface may be provided by one or more circles or holes of a known diameter. This is particularly useful in the identification of non-conformities on the curved surface of an object, such as a crack, a tear, a stain or a smudge, having a two-dimensional spread.

In a particularly preferred embodiment of the invention, the tool comprises a suitable active optical device 3. For example, this may be a camera, a charge coupled device (CCD) or other optical sensor for assisting in the visual quality assessment or for performing an automatic or semiautomatic quality assessment or parts thereof.

The invention will now be further described, by way of example, with reference to the accompanying drawings, in which:

FIG. 1 shows a longitudinal cross-section through a tool according to a preferred embodiment of the invention;

FIG. 2 shows an end view of the tool of FIG. 1; and

FIGS. 1 and 2 show a tool 2 according to a preferred embodiment of the invention for the identification of non-conformities on the circumferential surface of a cigarette.

Figure 3:
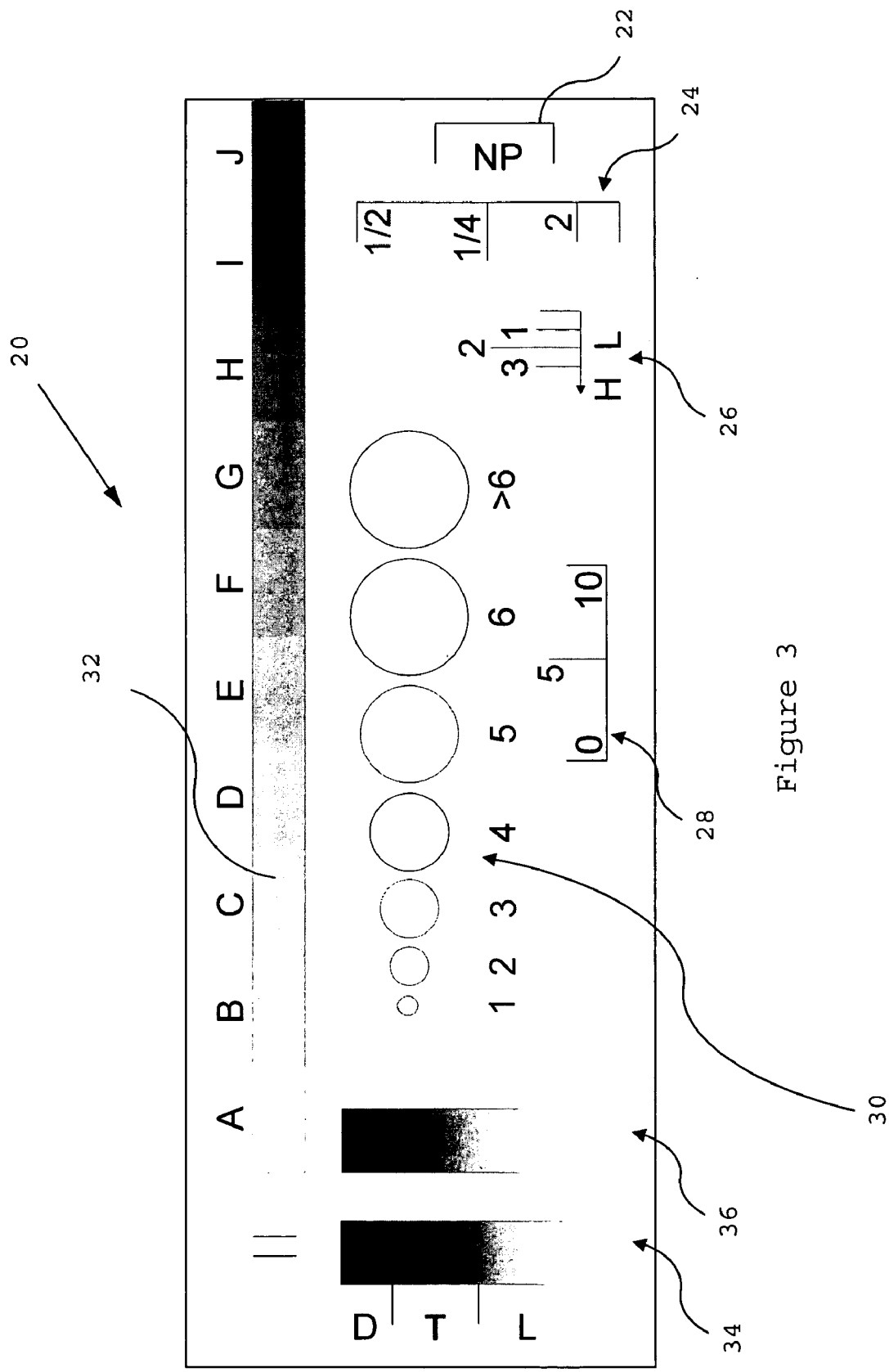
FIG. 3 shows a diagrammatic plan view of the surface of a transparent film forming part of the tool of FIGS. 1 and 2.

The tool 2 comprises an inner open-ended cylindrical tube 4 of circular cross-section having an internal diameter of 8.5 mm and an external diameter of 10 mm and a concentric outer open-ended cylindrical tube 6 of circular cross-section having an internal diameter of 10.5 mm and an external diameter of 12 mm. The inner cylindrical tube 4 and the outer cylindrical tube 6 are both 55 mm in length and are made from transparent plastic. These dimensions are most suitable for cigarettes with a circumference of 26 mm and a length of 105 mm. Slimmer cigarettes may require a slimmer tube for optimal measurement and shorter cigarettes may be handled better using a shorter tool. An integral funnel 10, having a maximum diameter of 14 mm, is provided at one end 12 of the outer cylindrical tube 6. The end 14 of the inner cylindrical tube 4 coinciding with the funnelled end 12 of the outer cylindrical tube 6 is also provided with an integral funnel 16 having a maximum diameter of 12 mm, which is concentric with the funnel 10 of the outer tube 6. Both funnels 10, 16 are 5 mm in length, so that the total length of the tool 2 is 60 mm. The inner 4 and outer 6 tubes are rotatable relative to each other and may be easily separated if required. During use of the tool 2, a cigarette is inserted through the funnels 10, 16 into the inner tube 4 and the position of the cigarette then adjusted by rotating the tubes 4, 6 relative to each other or by extending the inner tube 4 out from the outer tube 6 by an appropriate distance. In an alternative embodiment of the invention, the inner tube 4 and the outer tube 6 are affixed to each other. In this embodiment the tool is translated and rotated in its entirety relative to the cigarette to align a given area of interest with a desired scale.

As shown in FIG. 2, a 1 mm gap exists between the inner tube 4 and the outer tube 6 into which is introduced a transparent film 20 providing one or more scales for the identification of non-conformities. An example of a suitable transparent film 20 is shown in FIG. 3. The transparent film 20 is shown flat in the figure, but in use will be rolled up and inserted into the space between the inner and outer tubes 4, 6. The film 20 may be fixed to the surface of one of the tubes 4, 6, for example using an adhesive, although fixing is not required and may not be desired if it is intended to interchange different transparent films.

The transparent film 20 shown in FIG. 3 provides a number of different scales for the measurement of the size or extent or of the colour of an area of interest on the surface of a cigarette. The scale 22 consists of two markings 5.5 mm apart and once the film 20 is fitted between the tubes, the scale 22 extends circumferentially around the surface of the inner tube 4 and is located at one of the ends of the tube. The scale 22 may be used, for example, to assess a cigarette whose end has been flattened due to radial compression. A cigarette having a flattened portion which extends further than 5.5 mm circumferentially around the rod will be rejected.

The scale 24 consists of three markings, the first and second of which are 2 mm apart and the third of which is spaced from the first by a distance corresponding to half of the circumference of a conventional cigarette (13 mm). Once the film 20 is fitted between the tubes, the scale 24 extends circumferentially around the surface of the tube. The scale 24 may be used, for example, to assess a cigarette which has been improperly cut, resulting in ragged paper at the end of the rod. The cigarette may be classified depending on the circumferential extent of the ragged paper at the end of the rod, for example, if the ragged paper extends more than 2 mm around the circumference but less than halfway around the circumference, the non-conformity may be classified as low. If the ragged paper extends more than halfway around the circumference, the non-conformity would be classified as high. Such a classification may be used, for example, to decide on a course of action in response to the specific classification of the non-conformity.

The scale 26 consists of a series of millimetre ruler markings between 0 mm and 3 mm, which, once the film is fitted in between the tubes extends in a longitudinal direction along the surface of the tube. The scale 26 enables the identification of a number of different non-conformities. For example, a non-conformity related to the length of a tear or hole in the cigarette paper, or the length of a tear at the end of the rod, or the length of a flag of cigarette paper at the end of the rod, or the dimensions of a stain or smudge. The acceptable range of values for each of these non-conformities will vary, depending on the nature of the non-conformity.

The scale 28 consists of a series of 5 mm markings between 0 mm and 10 mm, which, once the film is fitted in between the tubes extends in a longitudinal direction along the surface of the tube. The scale 28 may be used in the same way as scale 26, discussed above, but in cases where a larger scale is appropriate.

The circumferential scales 22, 24 may be used in combination with the longitudinal scales 26, 28 in order to assess the extent of an area of interest in both the circumferential and longitudinal directions.

The scale 30 consists of a series of seven circles which have diameters of 1 mm, 2 mm, 3 mm, 4 mm, 5 mm, 6 mm and 6 mm, respectively. The second 6 mm circle is labelled ">6 mm". The circles may be used to measure the extent of a wide variety of non-linear areas of interest, whereby the extent of the area of interest may be determined by finding the circle whose size most closely corresponds to the size of the area of interest. Alternatively, a non-conformity is identified if the area of interest is larger than the circle representing the upper limit of the pre-determined quality requirements.

Alternatively a more precise assessment may be made. For example if a given area of interest has a spread that cannot be encircled by a 5 mm circle, but can be encircled by the 6 mm circle, the area of interest could be classified as being in the range of 5 mm to 6 mm. The second 6 mm circle may also be used to classify an area of interest that has a spread exceeding the area of the 6 mm circle. Examples of non-conformities which may be identified using the scale 30 include a hole, stain or tear in the cigarette paper, and smears or missing portions in a printed logo thereon. In alternative embodiments of the invention, the scale 30 may, for example, consist of a series of six circles which have diameters of 1 mm, 2 mm, 3 mm, 4 mm, 5 mm and 6 mm, respectively, and the 6 mm diameter circle may be used for classifications "<6 mm", "5 mm to 6 mm" and ">6 mm". The scale 30 may alternatively be provided by a series of holes in the film, having the same diameters as the circles previously described.

The transparent film 20 shown in FIG. 3 also provides a number of colour scales for the identification of non-conformities in the colour of the cigarette surface. Scale 32 is a gradual spectrum of colours ranging from yellow to brown that is divided into ten different bands, labelled alphabetically by the letters A to J in FIG. 3, from light to dark; scale 32 is shown in grey scale in FIG. 3. The spectrum may be used, for example, to assess the colour of cigarette paper or to assess stains on the cigarette paper in order to determine the level of contrast between the stain and the background. An area of interest on the circumferential surface of the cigarette may be classified depending on which of the bands A to J the colour of the area of interest most closely matches. For example, in the spectrum shown in FIG. 3, band J may be chosen as the target colour for the area of interest. An area of interest of a colour which matches band H or I may be classified as acceptable, an area of interest of a colour which matches any of the bands E to G may be classified as a low non-conformity, and an area of interest of a colour which matches any of the bands A to D may be classified as a high non-conformity. The identification of either a low non-conformity or a high non-conformity would lead to rejection of the cigarette, since it does not conform to the desired quality requirements. The distinction between low and high non-conformity may be used for additional calculations to evaluate the quality of the cigarette, for example to improve the production process. For this, the different levels of non-conformity might be weighted differently.

Scale 34 is a continuous grey scale, ranging from white at one end to black at the other. Limits on the side of the scale 34 indicate which grey levels are acceptable and which grey levels may be regarded as a non-conformity. In FIG. 3 the letter D indicates a dark non-conformity, L indicates a light non-conformity and T indicates the target colour. The scale 34 may be used to assess any printing, for example a logo, applied to the cigarette paper. A cigarette on which the logo is too faint, for example, will be rejected. The grey scale 34 may also be used to assess ink stains or smudges on the cigarette paper, for example, to compare the shade of an ink stain or smudge with the shade of the paper to determine the level of contrast between the stain and the background.

Scale 36 is a continuous scale of shades of red (which is shown in grey scale in FIG. 3). The scale 36 may be used to assess any red printing, for example in a logo, in an analogous way to scale 34. Different colour scales may be provided, depending on the colours used in any printing on the surface of the cigarette.

The combination of the different types of scales on a single transparent film enables a large number of possible types of non-conformities on the cigarette to be identified and assessed without the need to use different tools, or to interchange films between assessments.

In use, a cigarette having an area of interest on its circumferential surface is inserted into the inner tube 4 through the funnelled open end 12. The inner tube 4 and the outer tube 6 are rotated relative to each other and if necessary, the cigarette or the inner tube 4 is longitudinally adjusted relative to the outer tube 6 in order to align the area of interest with the appropriate scale. Alternatively, if inner tube 4 and outer tube 6 are affixed to each other, the tool 2 and the cigarette are rotated and translated relative to each other in order to align the specific scale with the corresponding area of interest. If the size of the area of interest is to be assessed, the area of interest is compared with the appropriate scale or scales in order to determine the circumferential and/or longitudinal extent of the area of interest. A quantitative measurement of the size of the area of interest may be taken, or the area of interest may be classified based on its level of acceptability, using a series of threshold values. If the colour of the area of interest is to be assessed, the area of interest is compared with the appropriate colour scale and the colour of the area of interest is matched with a colour in the spectrum. In use, the area of interest and the colour scale 32, 34, 36 are moved relative to each other along the colour scale 32, 34, 36 to match up the colours of the colour scale 32, 34, 36 and the colour on the cigarette. As with the size assessment, an absolute measurement of the colour of the area of interest may be established, or the area of interest may be categorised based on its level of acceptability, using a series of threshold values. Alternatively the scales 22, 24, 32, 34, 36 may be used to make a simpler yes/no assessment of whether the inspected area is a non-conformity. For example, if in the visual quality audit a stain of 3 mm or less in size is considered to be acceptable, any stain on the cigarette may be compared with the 3 mm circle of scale 30 in order to determine whether it is smaller or greater than 3 mm in size. This comparison enables an assessment of whether the cigarette meets the quality requirements, without the exact measurement of the size of the stain. For another non-conformity the acceptable size may be different and a different circle of scale 30 is used. If the cigarette has more than one area of interest on its surface, it may be realigned following assessment of each area of interest, in order to line up any further areas of interest with the appropriate scale. Once all of the area of interest have been assessed and all non-conformities have been identified, the cigarette is removed from the tube.

It will be appreciated that, while the embodiment described is intended for identifying a non-conformity on the circumferential surface of a cigarette, the same or similar tools may be used for identifying non-conformities on the surface of any cylindrical object.

While in the embodiment described the tool comprises a cylindrical tube for identifying non-conformities on the circumferential surface of a cylindrical object, it will be appreciated that the curved surface of the tool may be provided in different forms and with different curvatures and it will be apparent to the skilled man how the described tool could be adapted to make a tool for identifying non-conformities on any curved surface.

While in the embodiment described, particular size and colour scales are described, it will be appreciated that other types of scale could be provided on the curved surface of the tool depending on the object on which the tool is intended to be used and depending on the kind of non-conformity to be identified during a visual quality audit.

It will be appreciated that, while in the embodiment described, the tool comprises two concentric cylindrical tubes, a tool according to the invention may have only one cylindrical tube. It will also be appreciated that, while in the embodiment described the scales are provided on a transparent film which is inserted between the two tubes, the scales may be provided in a different form, for example, directly on the curved surface of the tool.

The invention claimed is:

1. A tool identifying a non-conformity on a curved surface of an object comprising: a cylindrical tube having a curved circumferential surface having a scale extending in a direction of curvature in a lateral direction, the scale enabling a measurement in the direction of curvature; and a viewing portion associated with the scale through which, in use, at least part of the curved surface of the object being identified is visible, the object extending in a longitudinal direction with reference to the scale.

2. A tool according to claim 1 having at least one size scale for assessing the size of an area of interest on a curved surface of an object.

3. A tool according to claim 1 having at least one colour scale for assessing the colour of an area of interest on the curved surface of the object.

4. A tool according to claim 1 comprising: the cylindrical tube with the curved circumferential surface having the scale extending along the direction of curvature, the scale enabling a measurement along the direction of curvature, and an open end into which, in use a cylindrical object may be inserted; and a viewing portion associated with the scale through which, in use, at least part of the curved circumferential surface of the cylindrical object inserted into the tube is visible.

5. A tool according to claim 4 wherein the open end of the tube is funnelled.

6. A tool according to claim 4 comprising a pair of concentric circularly cylindrical tubes.

7. A tool according to claim 6, wherein the tubes are rotatable relative to one another.

8. A tool according to claim 4 wherein the curved surface has at least one scale extending in a longitudinal direction of the tube.

9. A tool according to claim 1 having a size scale comprising a plurality of distance markings.

10. A tool according to claim 1 having a size scale comprising a plurality of circles of different diameter, preferably a plurality of circular holes through the curved surface of the tool.

11. A tool according to claim 1 wherein the viewing portion of the curved surface is transparent.

12. A tool according to claim 1 wherein substantially the entire curved surface of the tool is transparent.

13. A tool according to claim 1 wherein the tool comprises an active optical device.

14. A tool according to claim 1 sized to accommodate the circumferential surface of a cigarette.

15. A tool identifying a non-conformity on a curved surface of an object comprising: a tubular housing including a curved generally cylindrical surface with a curvature, having a scale extending in the direction of curvature in a lateral direction, the scale enabling a measurement in the direction of curvature; and a viewing portion associated with the scale through which, in use, at least part of the curved surface of the object being identified is visible, the object extending in a longitudinal direction with reference to the scale.

* * * * *